US00PP14405P39

(12) United States Plant Patent
Murakami

(10) Patent No.: US PP14,405 P3
(45) Date of Patent: Dec. 23, 2003

(54) PETUNIA PLANT NAMED 'SUNBELBURA'

(50) Latin Name: *Petunia hybrida*
Varietal Denomination: c.v. Sunbelbura

(75) Inventor: Yasuyuki Murakami, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 10/107,182

(22) Filed: Mar. 28, 2002

(65) Prior Publication Data

US 2003/0188365 P1 Oct. 2, 2003

(51) Int. Cl.[7] ..... A01H 5/00
(52) U.S. Cl. ..... Plt./356
(58) Field of Search ..... Plt./356

(56) References Cited

U.S. PATENT DOCUMENTS

| | | | |
|---|---|---|---|
| PP6,899 | P | 7/1989 | Tsuda et al. |
| PP6,914 | P | 7/1989 | Tsuda et al. |
| PP6,915 | P | 7/1989 | Tsuda et al. |
| PP8,489 | P | 12/1993 | Hirabayashi et al. |
| PP8,768 | P | 6/1994 | Hirabayashi et al. |
| PP9,322 | P | 10/1995 | Tachibana et al. |
| PP9,341 | P | 10/1995 | Tachibana et al. |
| PP9,342 | P | 10/1995 | Sakazaki et al. |
| PP9,556 | P | 5/1996 | Tachibana et al. |
| PP9,557 | P | 5/1996 | Suzuki et al. |
| PP9,754 | P | 12/1996 | Suzuki et al. |
| PP10,045 | P | 9/1997 | Rother |
| PP10,278 | P | 3/1998 | Murakami |
| PP10,279 | P | 3/1998 | Murakami |
| PP10,287 | P | 3/1998 | Murakami |
| PP10,310 | P | 3/1998 | Sakazaki |
| PP10,330 | P | 4/1998 | Sakazaki |
| PP10,355 | P | 4/1998 | Murakami |
| PP10,904 | P | 5/1999 | Hansson |
| PP11,006 | P | 7/1999 | Danziger |
| PP11,352 | P | 4/2000 | Murakami |
| PP11,558 | P | 10/2000 | Murakami |
| PP12,101 | P2 | 9/2001 | Sakazaki |

*Primary Examiner*—Anne Marie Grunberg
(74) *Attorney, Agent, or Firm*—Burns, Doane, Swecker & Mathis, L.L.P.

(57) ABSTRACT

A new and distinct variety of Petunia plant having a decumbent growth habit is provided. The Petunia plant has abundant branching particularly with respect to the secondary branching and a great profusion of blooms with the entire plant remaining in bloom for a considerable period of time. The flowers are very small with petals having a pale purplish pink color with deep reddish purple veins, and are abundantly formed in a spike. The blooming period commonly is from May to October. The plant also exhibits high resistance to rain, cold, heat, pests and diseases.

2 Drawing Sheets

Botanical/commercial classification: Petunia hybrida/Petunia Plant.
Varietal denomination: cv. 'Sunbelbura'.

BACKGROUND OF THE VARIETY

The Petunia is a very popular plant that is used for flower bedding and potting in the summer season. There are only a few varieties of the Petunia varieties which do not have an upright growth habit and which have a high resistance to rain, heat, cold and diseases. Recently, there were developed series of small-flowered Petunia varieties, such as 'Suntory SP-R' (U.S. Plant Pat. No. 9,557), 'Sunberubu' (U.S. Plant Pat. No. 9,754), 'Sunbelochipi' (U.S. Plant Pat. No. 10,355), and 'Sunbelki' (U.S. Plant. Pat. No. 11,558), having a semi-erect growth habit, short stems, a medium plant height, abundant branching, and a high resistance to heat, cold and rain. However, there are only a few Petunia varieties having a great profusion of flowers, a pale purplish pink flower color, a very small flower size, and a high resistance to rain, heat, cold and diseases. Accordingly, this invention was aimed at obtaining a new variety having a pale purplish pink petals with deep reddish purple veins, and very small flowers combined with the above features.

The new variety of Petunia plant according to this invention originated as a spontaneous whole plant mutation of unknown causation of the 'Sunbelkupi' variety (U.S. Plant Pat. No. 10,287). The new variety of Petunia plant was discovered in view of the distinctive flower color during propagation of 'Sunbelkupi' variety in January 2000 at Yokaichi-shi, Shiga-ken, Japan. The discovered Petunia plant was propagated by the use of cuttings into 500 plants and then grown in pots on trial basis in greenhouses beginning in January, 2001. The botanical characteristics of the plant were examined, using a similar variety, 'Pearl Sky Blue' variety (non-patented in the United States) and the parent variety 'Sunbelkupi' variety for comparison. As a result, it was concluded that this Petunia variety is distinguishable from any other variety whose existence is known to me, and this new variety of Petunia variety was named 'Sunbelbura'.

In the following description, the color-coding is in accordance with The R.H.S. Colour Chart of The Royal Horticultural Society, London, England. A color chart based on The Japan Color Standard for Horticultural Plants (J.H.S. Color Chart) is also added for reference.

The main botanical characteristics of 'Pearl Sky Blue' variety are as follows:

Plant:

*Growth habit.*—Medium upright.
*Plant height.*—Approximately 14 cm.

*Spreading area of plant.*—Approximately 15–17 cm in diameter.
*Blooming period.*—April to September in the southern Kanto area, Japan.

Stem:
*Thickness.*—Approximately 2.7 mm.
*Pubescence.*—Dense.
*Branching.*—Abundant.
*Length of internode.*—Approximately 1.3 cm.

Leaf:
*Shape.*—Elliptic.
*Length.*—Approximately 5.5 cm on average.
*Width.*—Approximately 3.5 cm on average.
*Color.*—Strong yellow green (R.H.S. No. 144A, J.H.S. No. 3507).
*Thickness.*—Approximately 0.5–0.6 mm.
*Pubescence.*—Dense.
*Leaf attachment angle to stem.*—Horizontal to droopy.

Flower:
*Facing direction.*—Upward.
*Type.*—Single.
*Shape.*—Funnel-shape, with five fissures.
*Shape of petal tip.*—Obtuse.
*Waving of petal.*—Weak.
*Lobation of petal.*—Shallow.
*Diameter.*—Approximately 5.5 cm.
*Color.*—Petal: Strong purple (R.H.S. No. 83C, J.H.S. No. 8310).
*Bottom color of the corolla throat and the outside color of corolla tube.*—Light yellow green (R.H.S. No. 3D, J.H.S. No. 3304).
*Reproductive organs.*—1 normal pistil, and 5 stamens.
*Peduncle.*—Approximately 0.7–0.9 mm in thickness, and approximately 2.7 cm in length.
*Physiological and ecological characteristics.*—Moderate resistance to cold, heat, diseases and pests, and strong resistance to rain.

The main botanical characteristics of the petunia plant 'Sunbelkupi' variety are as follows:

Plant:
*Growth habit.*—Decumbent, with the stems hanging down when growing in a hanging pot.
*Plant height.*—Approximately 5.8–6.1 cm.
*Spreading area of plant.*—The stems extends to a length of approximately 18–19 cm from the base, and the spreading area of the plant is approximately 78–83 cm in diameter.
*Growth.*—Very vigorous with abundant branching, a great profusion of blooms, and the entire plant remains in bloom for a considerable period of time.
*Blooming period.*—April to late October in the southern Kanto area, Japan. The plant shape does not change throughout this period.

Stem:
*Thickness.*—Approximately 1.2 mm.
*Pubescence.*—Normal to sparse.
*Branching.*—Very abundant with the secondary branching being very strong.
*Length of internode.*—Approximately 1.3 cm.

Leaf:
*Shape.*—Lanceolate.
*Length.*—Approximately 3.5 cm.
*Width.*—Approximately 1.0 cm.
*Color.*—Dark olive green (R.H.S. No. 137B, J.H.S. No. 3707).
*Thickness.*—Approximately 0.2–0.3 mm.
*Pubescence.*—Few.
*Leaf attachment angle to stem.*—Slanted upward to horizontal.

Flower:
*Facing direction.*—Slanted upward to horizontal.
*Type.*—Single.
*Shape.*—Funnel-shape, with five fissures.
*Shape of petal tip.*—Somewhat retuse.
*Waving of petal.*—Weak.
*Lobation of petal.*—Very shallow.
*Diameter.*—Approximately 2.7–2.9 cm.
*Color.*—Petal: Vivid reddish purple (R.H.S. No. 74A, J.H.S. No. 9207).
*Bottom color of the corolla throat.*—Brilliant greenish yellow (R.H.S. No. 3A, J.H.S. No. 2905).
*Outside color of corolla tube.*—Pale yellow green (R.H.S. No. 1D, J.H.S. No. 3102) with moderate olive lines (R.H.S. No. 152B, J.H.S. No. 2710).
*Reproductive organs.*—1 normal pistil, and 5 normal stamens. Both normal.
*Peduncle.*—Approximately 0.7–0.8 mm in thickness, and approximately 1.8 cm in length.
*Physiological and ecological characteristics.*—High resistance to rain, heat, drought and pests. The resistance to rain and heat is especially strong.
*Fertility.*—Fertile but is self-incompatible.

This new variety of Petunia 'Sunbelbura' variety was asexually reproduced by the use of cuttings at Yokaichi-shi, Shiga-ken, Japan, and the homogeneity and stability thereof were confirmed. The characteristics of the new variety are reliably transmitted to subsequent generations by such asexual reproduction.

SUMMARY OF THE VARIETY

This new variety of 'Sunbelbura' variety has a decumbent growth habit with attractive distinctive very small flowers having pale purplish pink petals with deep reddish purple veins. The plant has abundant branching and a great profusion of blooms, with the entire plant remaining in bloom for a considerable period of time. The secondary branching is especially strong. The new 'Sunbelbura' variety has a brilliant greenish yellow base color of the corolla throat and the outside color of the corolla tube is pale yellow green. The plant is highly resistance to cold, rain, heat, drought, pests and diseases. The resistance to rain and heat is very strong.

BRIEF DESCRIPTION OF THE PHOTOGRAPHS

DETAILED DESCRIPTION OF THE NEW VARIETY

Figure 1:
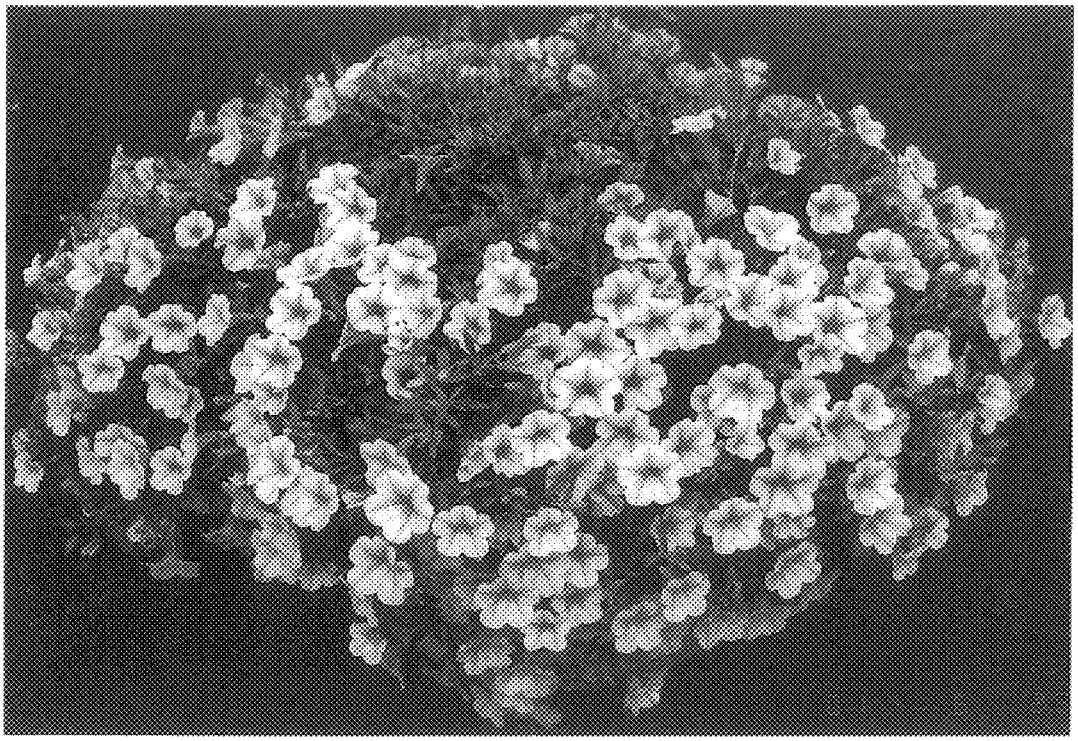
FIG. 1 shows the flowers and foliage of the new variety of Petunia plant.

The botanical characteristics of the new 'Sunbelbura' variety are set forth hereafter. The plants were observed during July at Yokaichi-shi, Shiga-ken, Japan. Young plants had been reproduced by the use of cuttings during June the year before.

Plant:

*Growth habit.*—Decumbent.

*Plant height.*—Very short, approximately 7 cm.

*Spreading area of plant.*—The stem commonly extends to a length of 20 cm from the base.

*Growth.*—Very vigorous with abundant branching, and a great profusion of blooms, and with the entire plant remaining in bloom for a considerable period of time.

*Blooming period.*—May to October in the southern Kanto area, Japan. This can be compared to a number of other Petunia varieties that commonly begin blooming a number of weeks earlier. The plant shape does not change throughout the blooming period.

Stem:

*Thickness.*—Thin, approximately 1.7 mm.

*Pubescence.*—Sparse to normal.

*Branching.*—Medium with a superior branching propensity. The secondary branches are particularly numerous.

*Length of internode.*—Short, approximately 1.4 cm.

Leaf:

*Shape.*—Lanceolate.

*Length.*—Very Short, approximately 3.4 cm.

*Width.*—Very Narrow, approximately 0.9 cm.

*Color.*—Moderate yellow green (R.H.S. No. 137B, J.H.S. No. 3712).

*Thickness.*—Thin, approximately 0.5 mm.

*Pubescence.*—Sparse.

*Leaf attachment angle to stem.*—Slanted upward to horizontal.

Flower:

*Facing direction.*—Slanted upward to horizontal.

*Type.*—Single.

*Shape.*—Funnel-shape, with five fissures.

*Shape of petal tip.*—Obtuse.

*Waving of petal.*—Weak.

*Lobation of petal.*—Very shallow.

*Diameter.*—Very small, approximately 2.9 cm.

Figure 2:
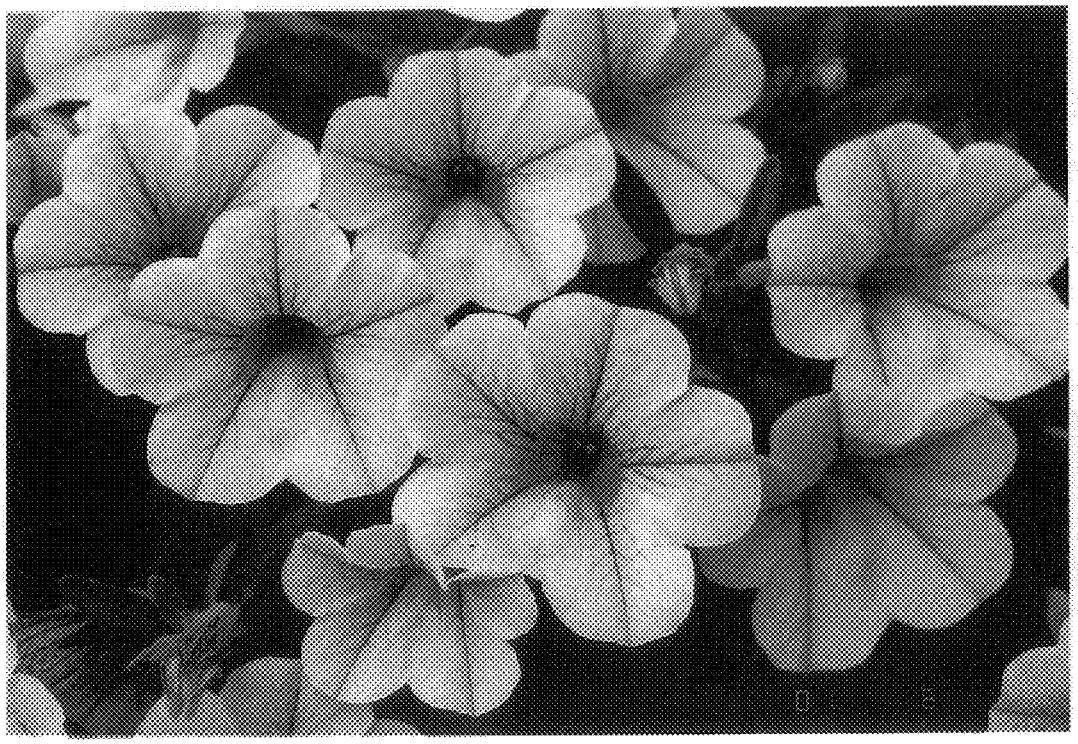
FIG. 2 shows a close view of the flowers of the new variety of Petunia plant.

*Variegated pattern of corolla.*—Present with distinct venation as illustrated in FIG. 2.

*Ground color of bi-colored petal.*—Pale purplish pink (R.H.S. No. 69B, J.H.S. No. 9202).

*Color of variegated pattern.*—Deep reddish purple (R.H.S. No. 77A, J.H.S. No. 9209).

*Base color of the corolla throat.*—Brilliant greenish yellow (R.H.S. No. 3A, J.H.S. No. 2905).

*Outside color of corolla tube.*—Pale yellow green (R.H.S. No. 1D, J.H.S. No. 3102).

*Reproductive organs.*—1 normal pistil, and 5 normal stamens.

*Fertility.*—Fertile, but self-incompatible.

*Fruit and seeds.*—The fruit is two-chambered and pyramidal in shape with rounded corners. Each side of the fruit commonly measures approximately 0.3, and the height from the base to the apex of the triangular shape commonly measures approximately 0.5 cm. The fruit coloration commonly is yellow-green, R.H.S. No. 144A. The seeds are globular in configuration, approximately 1.3 mm in diameter, a dark grayish-brown, R.H.S. No. 200A in coloration.

*Peduncle.*—Approximately 0.6 mm in thickness, approximately 1.5 cm in length, and R.H.S. No. 144A in coloration.

*Physiological and ecological characteristics.*—High resistance to cold, rain, heat, drought and diseases, such as Powdery Mildew. The resistance to rain and heat is very strong.

*Blooming.*—A bloom commonly lasts approximately 10 days on the plant and the duration is influenced by environmental conditions. Pinching is not necessary to ensure continued blooming; however, it does tend to enhance bloom production somewhat.

This new variety of Petunia plant is most suitable for flower bedding and potting, particularly in hanging pots and planters. It additionally is excellent for use as a ground cover.

I claim:

1. A new and distinct variety of Petunia plant, substantially as herein illustrated and described, characterized particularly as to novelty by (A) a semi-erect growth habit, (B) abundant branching with the secondary branching being particularly strong, (C) an abundant number of flowers in a spike with a great profusion blooms and the entire plant remaining in bloom for a considerable period of time, (D) a very small flower size with the petals having a pale purplish pink color with deep reddish purple veins, (E) a high resistance to rain, cold, heat, drought, diseases and pests, and (F) a late flowering time that commonly extends from May to October.

* * * * *